United States Patent [19]

Blatt et al.

[11] Patent Number: 5,200,325
[45] Date of Patent: Apr. 6, 1993

[54] SELF-INDICATING ANALYSIS EMPLOYING STOICHIOMETRIC CHEMICAL SUBTRACTION

[75] Inventors: Joel M. Blatt, Granger; Steven C. Charlton, Elkhart; Bert Walter, South Bend; Mary E. Warchal, Osceola, all of Ind.

[73] Assignee: Miles Inc., Elkhart, Ind.

[21] Appl. No.: 933,008

[22] Filed: Aug. 21, 1992

Related U.S. Application Data

[63] Continuation of Ser. No. 154,225, Feb. 10, 1988, abandoned.

[51] Int. Cl.$^5$ .................. C12Q 1/32; C12N 11/18
[52] U.S. Cl. ........................... 435/14; 435/25; 435/175; 435/26; 435/810
[58] Field of Search ............ 435/4, 14, 21, 25, 26, 435/28, 805, 810, 175; 422/56, 58; 436/66

[56] References Cited

U.S. PATENT DOCUMENTS

| | | | |
|---|---|---|---|
| 3,964,871 | 6/1976 | Hochstrasser | 23/253 |
| 4,490,465 | 12/1984 | Limbach et al. | 435/14 |
| 4,629,697 | 12/1986 | Limbach et al. | 435/26 |
| 5,032,506 | 7/1991 | Palmer et al. | 435/26 |

FOREIGN PATENT DOCUMENTS 8804694  6/1988  World Int. Prop. O. .

OTHER PUBLICATIONS

Bergmeyer, "Methods of Enzymatic Analysis", Second English Edition, Verlag Chemie GmbH, Weinheim/Bergstr, 1974 pp. 1415, 496, 468, 448, 655, 1663 and 574, vol. 1, 2, 3 and 4.

*Primary Examiner*—Robert J. Hill, Jr.
*Assistant Examiner*—Laurie Scheiner
*Attorney, Agent, or Firm*—Jerome L. Jeffers

[57] ABSTRACT

An analytical method and test composition for determining whether an analyte is present in a test sample at a predetermined concentration level by measuring or observing a preselected level of indicator response, e.g., color generation. A subtractive reaction is carried out on the test sample prior to the indicator reaction in order to stoichiometrically and specifically consume a predetermined amount of analyte. The resulting indicator reaction generates the preselected level of indicator response only if the analyte is present at the predetermined concentration level or greater. The subtractive reaction is enzymatically specific for the analyte in the reaction mixture and the amount of analyte consumed can be closely controlled by the amount of a regulating coreactant present at initiation. The method enables the determination of analyte without the need for standards or comparators, e.g., color charts, and therefore is self-indicating. In another embodiment, there is provided a method and test composition for improving an otherwise suboptimal assay response due to oversaturation of the response, e.g., color, generated by an indicator reaction.

9 Claims, 7 Drawing Sheets

SELF-INDICATING ANALYSIS EMPLOYING STOICHIOMETRIC CHEMICAL SUBTRACTION

This is a continuation, of application Ser. No. 07/154,225, filed Feb. 10, 1988, now abandoned.

BACKGROUND OF THE INVENTION

This invention relates to analytical methods for determining the presence of an analyte at a predetermined concentration in a test sample. More particularly, the invention concerns such a determination wherein the presence of the analyte at or above the concentration of interest is indicated by the appearance of a preselected spectrophotometric response, such as the appearance of color. Such determination is accordingly self-indicating because comparators or standards are unnecessary. In a further embodiment, the invention concerns visually read assays requiring optimization of color resolution of the indicator response over the range of analyte concentrations of significance.

Test methods are well known for determining the concentration of an analyte in a liquid test sample based on a spectrophotometric response produced by chemical reaction between the analyte of interest and an appropriate reagent/indicator system. The spectrophotometric response is usually a color change that is measured instrumentally or visually observed. Conventional tests provide quantitation of the amount or concentration of analyte in the sample by comparison of the test response to standard responses produced by known concentrations of analyte. Again, the comparison may be performed with a spectrophotometer or by visual comparison to a color chart.

Reagent strips are a common form of test device for performing these types of analyses. These devices have a handle or support means to which is attached a carrier member or matrix such as filter paper, polymeric film, or the like, which is incorporated with the reagent/indicator components in a dry state. Contact with the liquid test sample rehydrates the test composition and initiates the assay reaction. The spectrophotometric response generated from the carrier member is then related to standards to give an indication of analyte concentration in the sample tested.

These test methods and devices are useful in a variety of fields where the quantitative or qualitative measurement of substances in liquid samples is of importance. The testing of biological fluids for medical and veterinary purposes, foods and beverages, environmental and waste waters are representative. Reagent strips are particularly well-known as useful aids in medical diagnosis, from the self-monitoring of blood glucose levels by diabetic individuals to routine urinary metabolite screening and quantitative blood chemistry analysis in physician's offices and clinical laboratories.

While the test results provided by these prior art methods and devices provide sufficient quantitation to serve as useful means of analysis, and the reagent strip configuration is particularly attractive because of its simplicity and ease of storage and use, the precision of such tests is limited by the need to make comparisons to standards. Particularly where the response is a color change and the comparison is made visually, the limited ability of the human eye to resolve small differences in color can introduce an undesirable error factor into quantitation. Furthermore, where the colors generated by the indicator reaction over the range of analyte concentrations of interest are highly saturated in hue, visual resolution for quantitation purposes can be significantly below optimal levels.

There are a number of attempts in the literature to devise quantitative test systems that would be self-indicating. By this is meant a test system that would provide a relatively unambiguous yes/no response or indication at a prescribed analyte concentration. Thus, if the programmed indicator response is observed, such as visual detection of the appearance of color, the indication is that the analyte is present at the predetermined concentration or greater. While the principle of self-indication is well-known, the prior art is devoid of a practical approach to constructing a test system that would yield sufficiently unambiguous yes/no responses to be truly self-indicating.

One very early approach to making a self-indicating test system employed an antagonist substance in the composition which would act on the indicator to prevent color formation below a predetermined level of analyte (U.S. Pat. No. 2,893,844). Indicators that are susceptible to reaction with an antagonist substance will also be affected by a variety of nonspecific environmental factors such as interfering substances in the sample. Such systems therefore are not sufficiently reliable as quantitative tests. Other early approaches used the principle of limiting the amount of indicator in the test composition (U.S. Pat. No. 3,006,735) or physically limiting the amount of analyte reaching the test composition by semipermeable membranes (U.S. Pat. No. 3,723,064).

More recently a number of different approaches have been suggested. U.S. Pat. Nos. 3,964,871; 4,042,329, and 4,059,407 reemphasize the desirability of self-indicating test devices wherein a plurality of test areas are arranged to give detectable responses to different levels of analyte. However, the reaction schemes offered for accomplishing self-indicating responses have notable shortcomings. The principal scheme proposed is based on the prior known use of indicator antagonist or titrant substances, which leads to the problem of sample interferences. The evolution of indicators has been towards compounds of greater and greater stability against environmental factors. As a result, the currently preferred indicators are essentially nontitratable by antagonist compounds as proposed in the subject references. Another approach offered is the complexation of analyte to prevent reaction with the indicator system. The systems proposed are relatively nonspecific for the analyte, some are reversible complexations, and some produce undesirable precipitates. No data is provided and the systems are quite unrefined.

Another more recent approach is described in U.S. Pat. No. 4,234,313 which proposes the use of indicators that go from colored to colorless upon reaction with analyte. This approach has the key disadvantage of requiring the use of limited amounts of indicator because the complete consumption of indicator is required for the detectable color change to occur. As a result, the indicator reaction kinetics are slow. Further, assigning a colorless result to be a positive result is the reverse of what the typical technician is used to in the laboratory.

U.S. Pat. No. 4,654,310 proposes the use of a nonresponsive reaction that is competitive with the indicator reaction to effectively reduce the rate of indicator response at varying levels of analyte concentration. This reference teaches the use of a catalyst-controlled secondary reaction to effectively remove competitive amounts of analyte from the indicator reaction. Several test areas would be provided with varying amounts of the catalyst and excess amounts of the reactants of the secondary reaction so that the ability of the indicator reaction to produce a response, e.g., color, depends on the amount of analyte present. The most significant limitation of this approach is that since the indicator and secondary reactions kinetically compete for analyte, the slope of the indicator response curve is decreased with detrimental effects on the ability to discriminate indicator responses at all levels of analyte.

Accordingly, there continues to be a need for a self-indicating test system that is resistant to interferences in the test sample, that provides a stable, essentially irreversible indicator response, and that does not sacrifice resolution.

A further limitation of reagent strip test devices is their general lack of uniformly good instrumental or visual resolution over the entire range of analyte concentrations of analytical significance. While oftentimes resolution at the lower end of the concentration range can be quite good, quantitation by instrumental or visual means suffers at the upper end of the range. A common cause of this phenomenon is the oversaturation of the indicator response, e.g., color, at high analyte concentrations.

Accordingly, there is a further need for visually interpreted or instrumentally read test systems that can be adjusted to provide optimal resolution of the indicator response within the range of analyte concentrations of interest.

SUMMARY OF THE INVENTION

The present invention provides a means for providing a highly advantageous self-indicating test system as well as for adjustment of colorimetric test systems to provide optimal color resolution within a desired range of analyte concentrations. These attributes result from carrying out a stoichiometric analyte-specific subtractive reaction effectively prior to carrying out the indicator reaction. The controlled consumption of a predetermined amount of analyte in the test sample causes a shift of the indicator response curve such that the analyte concentration that yields a predetermined indicator response can be selected in advance to provide a self-indicating feature. Also, the shift in the response curve, particularly for visually read indicator reactions, can be used to optimize resolution of indicator response within a desired range of analyte concentrations.

By subtracting analyte from the reaction system essentially before the indicator reaction can occur results in an effective decrease in the amount of analyte that is detectable by the indicator response. If the subtractive reaction is controlled to consume a predetermined amount of analyte in the reaction mixture, then the point at which a particular level of response, such as the appearance of color, can thereby be controlled. Control of the subtractive reaction is achieved by employing an enzymatic reaction or sequence of reactions that is specific for the analyte in the reaction mixture and that involves a regulating coreactant such as a cosubstrate that is consumed along with the analyte in the subtractive reaction. The initial amount of coreactant present in the reaction mixture is selected to be stoichiometrically sufficient for consumption of the desired amount of analyte.

The stoichiometric subtraction of analyte prior to any substantial indicator reaction has the key advantage of not affecting the indicator response to the amount of analyte that remains after subtraction. Therefore, the slope of the indicator response curve is unchanged even though the curve itself is shifted to begin at a preselected analyte concentration. Because the slope is unchanged, resolution of the response at the threshold level in a self-indicating system, or throughout the range of analyte concentrations, e.g., in a visually read system, can be held at an optimal level for the indicator system employed. No prior art approach offers this feature.

The analyte can be a substance which is itself of analytical interest or can be an intermediate product formed by reaction of the principal substance of interest in a preliminary reaction. As the term will be used herein, the analyte is the substance upon which both the subtractive and indicator reactions act, and in practical test systems will often not be the primary substance of analytical interest, but rather an intermediate product such as an enzyme substrate or cofactor that participates in a variety of useful indicator and subtractive reactions, e.g., NADH, NADPH, glycerol, ATP, or hydrogen peroxide.

Numerous advantages result from the use of a stoichiometric subtractive reaction:

1. Stoichiometric subtraction does not change the magnitude of the range of optimal resolution, just its position. Thus, sensitivity (the slope of the dose response curve) is not altered as it is with kinetic partitioning. This results in reagent performance in which the range of optimal resolution of a system is shifted to progressively higher analyte concentrations in discrete jumps which depend directly on the amount of subtractive reagent added to the system. A test system designed in this way would comprise a series of tests, e.g., multiple reagent strip pads or cuvettes, each having only that useful range which the basic indicator response chemistry allows. Only the total system of pads or cuvettes would have an extended range.

2. An "all-or-none" invdication, as might be employed in a self indicating test ("yes-no" test), may be designed to be extremely sharp. In this case, the range of optimal resolution would be very narrow as, for example, by use of an indicator with extremely high molar absorbancy index. Very little judgement would thus be required to determine if a given threshold level of analyte has been exceeded.

3. The enzymatic nature of chemical subtraction as described herein confers specificity that will be far superior to simple chemical complexation schemes. Thus, fewer instances of interference would be expected to occur than might occur otherwise, resulting in general improvement in reliability and accuracy of the test system.

4. Because of the stoichiometric nature of chemical subtraction as described herein, temperature fluctuations will have very little effect on the system. Subtraction by kinetic partitioning between two competing reactions requires very carefully controlled conditions to be reproducible because it is based solely upon difference in rate. Temperature variations would be expected to change the proportion of analyte, or analyte equivalents, flowing into the alternate pathways. Thus, kinetic partitioning is not as inherently reliable as stoichiometric subtraction.

DESCRIPTION OF THE PREFERRED EMBODIMENTS

Figure 1:
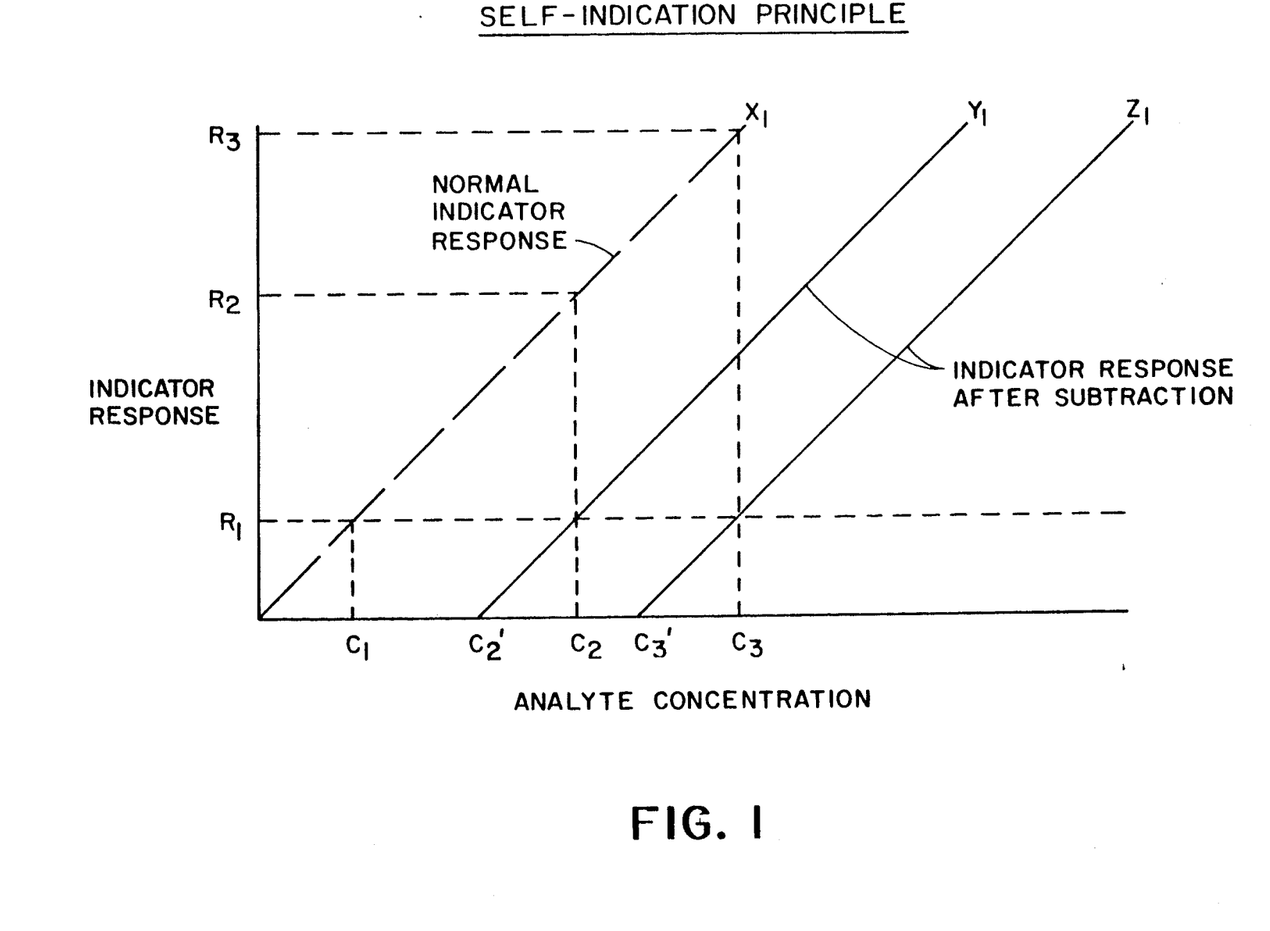
FIG. 1 is a graphical illustration of the self-indication principle of the present invention.
Figure 2:
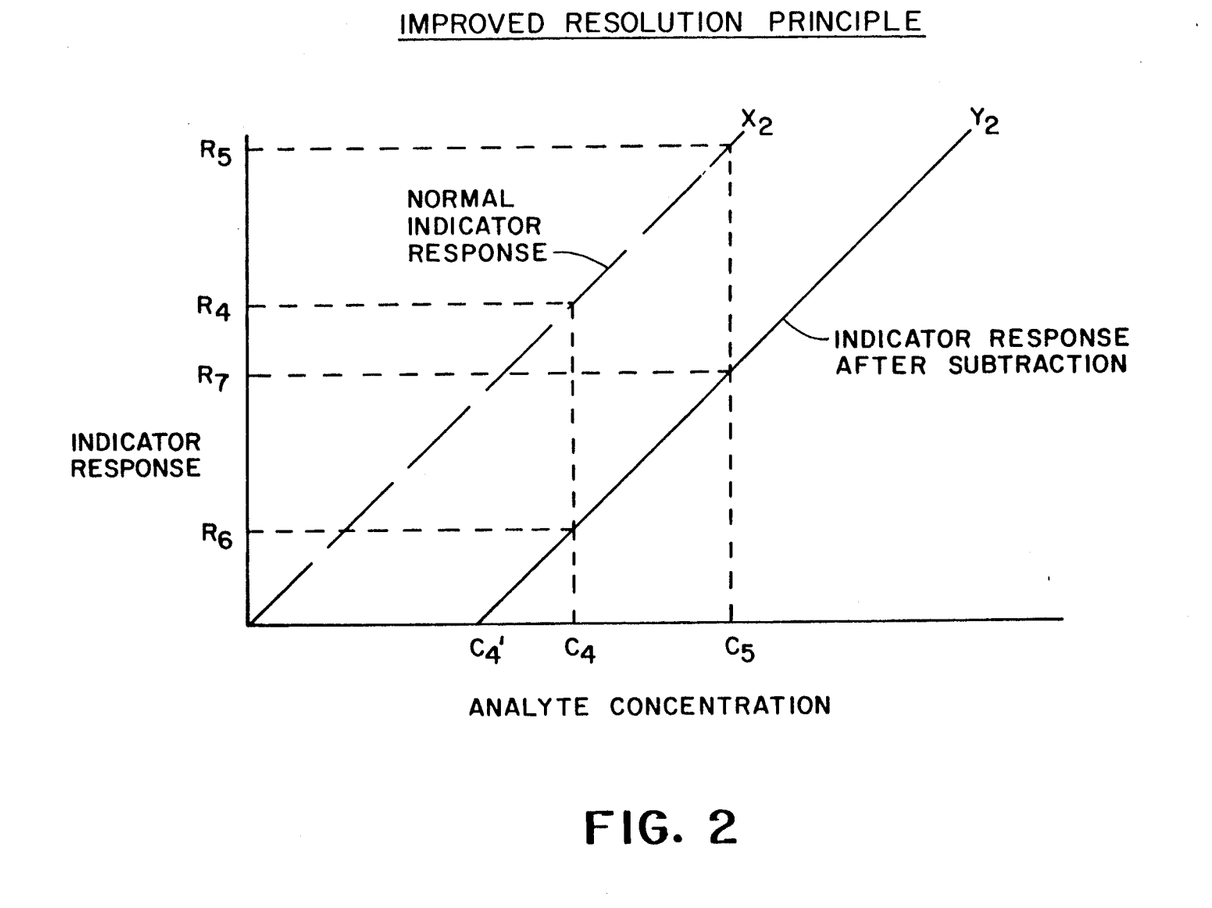
FIG. 2 is a graphical illustration of the improved resolution principle of the present invention.
Figure 3:
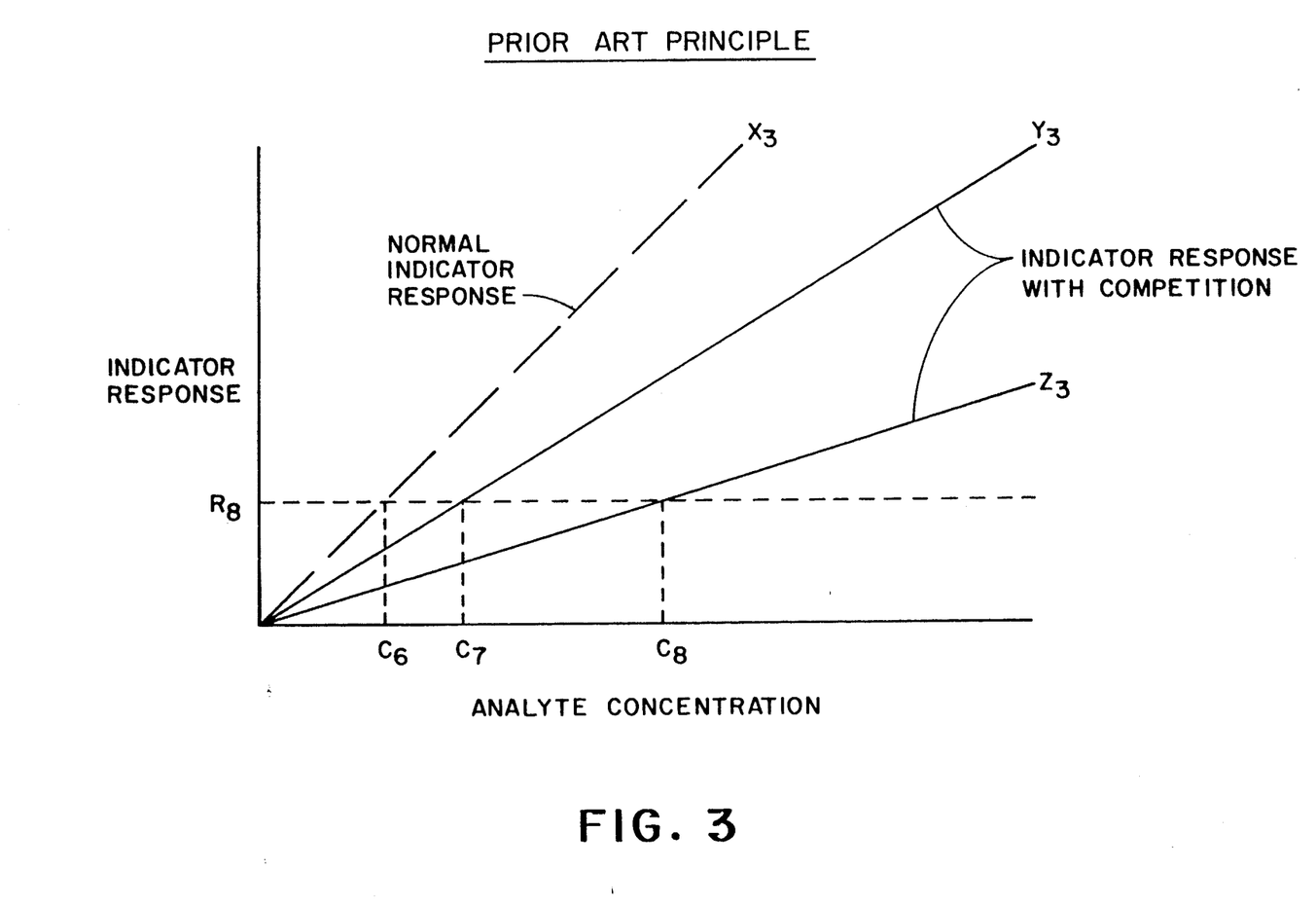
FIG. 3 is a graphical illustration of the principle of the prior art kinetic approach to self-indication.

The principles upon which the present invention operates can best be understood with reference to FIGS. 1-3 of the drawings. These figures are graphs representing illustrative indicator response curves.

Principle of Self-Indication

In FIG. 1, the normal indicator response to increasing levels of analyte is shown as upward sloping dashed line $X_1$. For illustration purposes, the indicator response will be a color change. The $R_1$ level of indicator response is the threshold level of detectability, e.g., the point at which the appearance of color can be detected visually. An analyte concentration in the test sample of $C_1$ provides this threshold indicator response. Using the normal indicator response, the ability to quantitate the $C_2$ and $C_3$ analyte concentrations depends upon the eye's ability to accurately distinguish colors $R_2$ and $R_3$ If the $R_2$ and $R_3$ responses are nearly indistinguishable because of a saturated color response, resolution of analyte concentrations $C_2$ and $C_3$ becomes extremely error prone.

The solid upward sloping lines $Y_1$ and $Z_1$ represent the indicator response shifted by two different subtractive reactions in accordance with the present invention. These response curves result from consumption of $C_2'$ and $C_3'$ amounts analyte in the subtractive reaction. As a result of the subtractive reaction, $C_2$ and $C_3$ respectively become the amount of analyte in the sample required to give the $R_1$ threshold indicator response.

Therefore, using shifted indicator response $Y_1$, the observation of the appearance of color means that the analyte is present in the test sample at concentration $C_2$ or greater. Likewise for response $Z_1$ and analyte concentration $C_3$.

If separate assays are performed using indicator responses $Y_1$ and $Z_1$ (accomplished by running separate reactions with subtraction of amounts $C_2'$ and $C_3'$ of analyte) and one simply observes whether color appears or not (a yes/no observation), the $C_2$ and $C_3$ concentration levels can be readily distinguished. This contrasts with the poor resolution possible using the normal indicator response $X_1$ and attempting to resolve colors $R_2$ and $R_3$. Moreover, the greatest resolving power exists at the threshold level of detection (the eye can resolve the appearance of color better than it can distinguish between different hues of color). Since this level of detection $R_1$ is the basis of quantitation using the subtraction-shifted indicator responses at all selected analyte concentrations (e.g., $C_2$ and $C_3$), the present self-indicating test system possesses maximum precision using the selected indicator system.

Principle of Improved Resolution

In addition to providing a means for self-indication, the present invention also provides a means for improving the quantitation over a range of analyte concentrations using a single indicator reaction.

In FIG. 2, the normal indicator response to increasing levels of analyte is shown again as upward sloping dashed line $X_2$. If the normal indicator response produces nearly saturated colors at levels $R_4$ and $R_5$, analyte concentrations $C_4$ and $C_5$ become difficult or even impossible to distinguish. Such an indicator response giving suboptimal or no resolution within the $C_4$–$C_5$ analyte concentration range can be adjusted in accordance with the present invention to provide optimal resolution over this concentration range of interest. By performing a stoichiometric subtraction reaction to consume $C_4'$ amount of analyte in the sample, the response curve shifts to solid line $Y_2$ to now give indicator responses from $R_6$ to $R_7$ over the $C_4$–$C_5$ analyte concentration range of interest. The $R_6$ to $R_7$ range of indicator response represents the region of optimal resolution of color changes. The indicator response is shifted to gain the benefit of such optimal resolving power by subtracting a $C_4'$ amount of analyte in accordance with the present invention.

Comparison to the Prior Art

FIG. 3 represents the kinetic competition approach to self-indication taught by U.S. Pat. No. 4,654,310. The normal response of the indicator system is shown as line $X_3$. A competitive secondary reaction is formed in separate reaction mixtures by adding varying amounts of a catalyst, and excess amounts of the secondary reactants, so that there is an ongoing consumption of analyte during the indicator reaction. The competitive reaction produces nonresponsive products resulting in a decreased slope of indicator response. Indicator responses $Y_3$ and $Z_3$ represent those responses resulting from the presence of two different levels of catalyst in the indicator reaction mixture. As a result, a self-indicating system is provided since the presence of $C_6$ concentration of analyte will provide threshold color production $R_8$ only in the reaction that shows indicator response $X_3$. Likewise, color is seen in reactions $X_3$ and $Y_3$ (but not $Z_3$) if the analyte is present in concentration $C_7$. Finally, analyte concentration $C_8$ gives color production in all three reaction systems. The problem that is readily seen, however, is that the determination of the appearance of threshold indicator response $R_8$ in the $Z_3$ reaction system is subject to increasing error because of the decreased slope of indicator response. Slight errors in detecting the appearance of the $R_8$ response lead to large errors in quantitation. A broad range of analyte concentrations in the region of $C_8$ gives nearly indistinguishable indicator responses. In comparison, referring back to FIG. 1, even at high analyte concentrations, e.g., at $C_3$, the present invention maintains the resolving power of the normal indicator response.

The Subtractive Reaction

The stoichiometric subtraction reaction of the present invention is intended to consume a predetermined amount of analyte in the test sample before measurement of the indicator response such as by the performance of an indicator reaction. Consumption of analyte is controlled and dictated by use of a reaction that is enzyme-catalyzed and involves at least one coreactant with the analyte. Such coreactant is herein referred to as the regulating coreactant because the amount of analyte consumed is dependent upon the amount of the coreactant present and its stoichiometric relationship to the analyte in the subtractive reaction. The subtractive reaction can be a single enzymatic reaction or a sequence of reactions at least one of which is enzymatic, preferably the initial reaction acting on the analyte, and in one of which a reactant can serve as the regulating coreactant.

The subtractive reaction consumes an amount of analyte that is stoichiometrically equivalent to the amount of coreactant which is present upon initiation of the subtractive reaction and is subsequently entirely consumed therein. In the simplest terms, the present invention can therefore be diagrammatically illustrated as follows:

Characteristics of the Subtractive Reaction

A principal characteristic of the subtractive reaction of the present invention is that it be substantially complete before measuring the indicator response to carrying out the indicator reaction. In this way, the subtraction of analyte is stoichiometric, not kinetic, and thus the slope of the indicator response is essentially unaffected. It is evident that there are a number of ways to carry out the subtractive reaction in order that it be completed before any significant indicator response can occur.

One approach is to carry out the subtractive reaction in the absence of one or more, or all, of the reagents of the indicator reaction. Upon completion of the subtractive reaction, the missing indicator reagents are added to initiate the indicator reaction. The same effect can be obtained by carrying out the subtractive reaction in the presence of all of the reagents of the indicator reaction where one or more of the indicator reagents are present in a modified form that is inactive in the indicator reaction. Upon completion of the subtractive reaction, the modified indicator reagent or reagents are transformed appropriately into the active form to initiate the indicator reaction. Modifications of indicator reagents to render them inactive for this purpose include microencapsulation, chemical derivatization or complexation, and like techniques known in the art.

It will normally be preferred that all of the indicator reagents be present in their fully active forms in the reaction mixture simultaneous with the performance of the subtractive reaction. The objectives of the present invention are obtained in this case by employing a subtractive reaction that is sufficiently fast that it is essentially complete before the indicator reaction can proceed to any significant extent. Since the subtractive reaction is enzyme-catalyzed, one selects an enzymatic reaction scheme based on an enzyme having a sufficiently high turnover rate and/or a $K_M$ that is readily exceeded in the reaction mixture so that the resulting subtractive reaction is very rapid compared to the indicator reaction. The coreactant or coreactants in the enzyme-catalyzed subtraction reaction will be present in excess of $K_M$, usually in 2-fold or greater excess of $K_M$, and preferably in 5-fold or greater excess of $K_M$, and/or the amount of enzyme present will be at sufficiently high levels that rapid reaction kinetics are produced.

It is also a principal characteristic of the subtractive reaction that it be effectively specific for the analyte in the reaction mixture in which the subtractive reaction is performed. The specificity of the subtractive reaction assures that the stoichiometric subtraction of analyte will not suffer significant sample interferences. In this way, the amount of analyte consumed by the subtractive reaction is quantitatively and reproducibly controlled by the amount of the regulating coreactant present.

The specificity of the subtractive reaction is dictated essentially by the specificity of the enzyme that catalyzes such reaction. It should be understood at this point that the specificity required for the present invention is not an absolute specificity against all other substances in nature, but rather specificity relative to the other substances present in the reaction mixture. It is only required that the analyte be essentially the only substance in the reaction mixture which can be consumed by the enzymatic reaction with the coreactant. Therefore, the enzymatic reaction selected to serve as the subtractive reaction will be chosen on the basis that there is no other substance normally present in the sample or other assay reagents that can substantially compete with the analyte for reaction.

A further characteristic of the subtractive reaction is that it act on the analyte and not on any indicator reaction product. By the term analyte is to be understood the substance that serves as the common reactant in both the subtractive and indicator reactions. In some cases, therefore, the analyte may not be the substance of actual analytical interest in the assay but rather an intermediate product formed by a preliminary reaction or reactions with the substance ultimately to be determined. Where the analyte is an intermediate product, it will preferably be a substance that is known to be a reactant in a variety of potentially useful subtractive and indicator reaction systems. In this way, the subtractive and indicator schemes which are optimized for the analyte can be used in a variety of assays. Such reaction schemes will be useful in determining substances that can be converted by specific preliminary reactions to products that include the analyte. The analyte when used in this sense can be termed a pivotal or common substrate and will include, without limitation, such substances as the nucleoside phosphates nicotinamide dinucleotide (NAD) and its reduced form (NADH), nicotinamide dinucleotide phosphate (NADP) and its reduced form (NADPH) flavin adenine dinucleotide (FAD), flavin mononucleotide (FMN), and the adenosine phosphates (AMP, ADP, and ATP); hydrogen peroxide; glycerol; and the like.

Another principal characteristic of the subtractive reaction is that the products which are produced do not exhibit any substantial indicator response. An essential feature is that the subtractive reaction consume a predetermined amount of analyte without generating any substantial indicator response, and further without interfering substantially with the indicator response or its generation. These considerations need be taken into account in designing and evaluating the reaction schemes to be used for the indicator and subtractive reactions respectively.

It is also particularly preferred that the subtractive reaction be essentially irreversible over the time period required for the indicator reaction to generate its detectable response. Otherwise it will be necessary to compensate for or factor in the amount of analyte that is regenerated by the reverse reaction. Optimally, the amount of analyte consumed by the forward subtractive reaction is not subject to reversal with time. Irreversibility can be attained by any available means for creating a large free energy change in forming the products of the reaction. This can be accomplished, for example, where one of the products of the subtractive reaction is a gas, an oxidation-reduction product, or other significant molecular modification. The use of mordants or other complexing agents that effectively withhold a product from participating in any reverse reaction is also contemplated. Irreversibility can also effectively be obtained by employing a subtractive reaction in which one of the reactants is present in extreme excess, e.g., water. Where enzymatic reactions are involved, systems can be selected in which the $K_M$ of the forward reaction is much less than the reverse reaction such that the enzyme is effectively tied up with the forward substrate.

Particular examples of assay systems comprising subtractive and indicator reactions will now be described.

A. Pyruvate/LDH subtraction of NADH

NADH is a common intermediate product in the enzymatic determination of substances of analytical interest. A particularly useful subtraction reaction is:

$$NADH + pyruvate \xrightarrow{LDH} lactate + NAD^+$$

which can be further modified to render the subtraction of NADH essentially irreversible by the reaction:

$$lactate + O_2 \xrightarrow{LOX} CO_2 + acetate$$

where LDH is lactate dehydrogenase and LOX is lactate 2-monooxygenase. Given favorable conditions, the overall subtraction reaction is capable of removing lactate as fast as it is produced from pyruvate, thus preventing reversal of the LDH reaction.

A number of preliminary reactions that produce NADH as a function of the presence of a particular substance of analytical interest can be coupled to this subtractive system for the purposes of the present invention, for example:

(a) $glucose + NAD^+ \xrightarrow{GDH} NADH + gluconolactone$ where GDH is glucose dehydrogenase, (b) $cholesterol\ esters \xrightarrow{CEH} cholesterol$ $$cholesterol + NAD^+ \xrightarrow{CDH} NADH + cholestenone$$

where CEH is cholesterolester hydrolase, and CDH is cholesterol dehydrogenase, (c) $triglycerides \xrightarrow{lipase} glycerol + free\ fatty\ acids$ $$glycerol + ATP \xrightarrow[Mg^{+2}]{glycerol\ kinase} glycerol\text{-}3\text{-}phosphate + ADP$$

$$glycerol\text{-}3\text{-}phosphate + NAD^+ \xrightarrow{GPDH} NADH + dihydroxyacetone\text{-}3\text{-}phosphate$$

where GPDH is glycerol3-phosphase dehydrogenase, (d) $ethanol + NAD^+ \xrightarrow{alcohol\ dehydrogenase} NADH + acetaldehyde$ Likewise, NADH partipates in a number of useful indicator reactions which can act on the remainder from the subtractive reaction. NADH indicators include iodonitrotetrazolium chloride (INT), nitroblue tetrazolium chloride (NBT), and dichloroindophenol (DCIP). NADH can also be determined by the lipoamide system involving the reactions:

$$lipoamide\ (disulfide) + NADH \xrightarrow{LADH} reduced\ lipoamide + NAD^+$$

$$reduced\ lipoamide + disulfide\ indicator \longrightarrow lipoamide + color$$

where LADH is lipoamide dehydrogenase and disulfide indicators include such reagents as dithio-(bis-nitrobenzene) (Ellman's reagent) or any of the other conventional indicators of this type.

B. α-Ketoglutarate/glutamate dehydrogenase subtraction of NADH

This subtractive system is based on the reaction:

$$\alpha\text{-}ketoglutarate + NADH + NH_4^+ \xrightarrow{glutamate\ dehydrogenase} glutamate + NAD^+$$

In the presence of excess $NH_4^+$, this reaction can become essentially irreversible. Further irreversibility can be obtained by adding the reaction:

$$glutamate \xrightarrow{glutamate\ decarboxylase} 4\text{-}aminobutyrate + CO_2$$

The preliminary and indicator reactions described in (A) above will apply to this subtractive system as well.

C. Lipoamide/lipoamide dehydrogenase subtraction of NADH

Another useful subtraction reaction for NADH is based on the lipoamide (DL-6,8-thioctic acetamide) chain of reactions:

lipoamide (reduced form)

which can be rendered irreversible by converting lipoamide back to its oxidized form, e.g., lipoamide (reduced) + disulfide acceptor → lipoamide (oxidized) + acceptor (reduced)

The disulfide acceptors are selected from those compounds which accept electron equivalents from lipoamide without producing a color change, e.g., 2,2'-dithio-bis(pyridine-N-oxide) (DTPO).

A similar reaction is the reaction of glutathione and NADH in the presence of glutathione reductase.

D. Glyceraldehyde-3-phosphate/α-glycerolphosphate dehydrogenase subtraction of NADH A further scheme for subtracting NADH is provided by the sequence:

NAD$^+$ + α-glycerolphosphate wherein α-GPD is α-glycerolphosphate dehydrogenase. The above reaction can be further refined to provide irreversibility by the reaction:

glycerol + inorganic phosphate

Again, the preliminary and indicator reactions that produce and detect NADH, respectively, as described in (A) above will apply to this subtractive system.

E. ATP/hexokinase subtraction of glucose

A subtractive reaction that can be applied directly to glucose as the analyte is:

Hexokinase can also be replaced with glucokinase. If the presence of ADP can lead to possible interference in the overall assay system, it can be effectively removed by the reaction:

AMP is normally non-reactive with ATP-dependent reactions such as bioluminescene. The indicator reaction for glucose could then be:

with NADH being detected with any of the indicator reactions described above.

F. Glucose/hexokinase subtraction of ATP

The reverse of the immediately preceding subtractive system can also be used, i.e., to subtract ATP with glucose as the regulating coreactant.

Preliminary reactions that produce ATP as a function of a particular substance of analytical interest and that can be coupled to this subtractive reaction include:

Indicator reactions for ATP include the well-known bioluminescence schemes as well as color-generating systems such as:

NADH ⟶ color, as above.

G. Glycerol/glycerol kinase subtraction of ATP

Another approach to subtracting ATP is based on the reaction:

H. ATP/glycerol kinase subtraction of glycerol

The subtraction of glycerol can be accomplished through the reaction shown in (F) above as well. Glycerol can be generated from triglycerides in a preliminary reaction and can be detected with glycerol dehydrogenase/NADH indicator systems as described above.

The indicator response can be essentially any analytically detectable response, particularly chemical or electrical in nature. Chemical properties of the analyte or a reaction product of an indicator reaction are normally used as the indicator response, particularly physiochemical properties such as the optical or electrochemical properties of a compound. Useful optical properties are fluorescence, light absorbance, particularly in the visible and ultraviolet ranges, visually detectable color changes, e.g., the appearance of color or changes in hue or saturation, and luminescence, e.g., chemiluminescence or bioluminescence. Detection of the indicator response will depend upon the nature of the response.

Instrumental detection, such as with fluorometers, photometers, spectrophotometers, colorimeters and the like, will often be employed. Visual observation of color changes is particularly enhanced by the present invention, as well as instrumental measurements of changes in light absorbance in the visible and/or ultraviolet range, and especially by reflectance photometry.

In regard to colorimetric indicator responses useful in the self-indicating embodiments of the present method, the use of a subtractive reaction to adjust the relative position of the appearance of threshold color to a desired level of analyte allows the indicator product to be selected from a wide range of materials. Those dyes or indicators which would otherwise be unsuitable for use in quantitation because of their high molar extinction coefficient are rendered quite useful, and in fact are preferred, in the present self-indicating method. Because such materials produce intense colors in response to analyte, the threshold appearance of color is rendered quite readily detectable and therefore the precision of the assay result is improved.

It is contemplated that although the present method offers significant advantages in analytical systems that employ a separate indicator reaction to produce a product exhibiting the indicator response, in some cases it is possible to measure a physical property of the analyte itself as the indicator response. This is particularly applicable where the analyte is an intermediate product such as NAD, NADH, NADP, or NADPH which can be measured directly by its characteristic absorbance properties.

Assay Method and Test Formats

In performing the present method, the subtractive reaction is first carried out to substantial completion and thereafter the indicator reaction is performed. As described above, this can be done by actually delaying the addition or contact of the indicator reagent or reagents until the completion of the subtractive reaction or by selecting conditions and reaction schemes which effectively sequence the reactions due to their relative kinetics. Although sequential timed additions of the subtractive and indicator reagents will of course accomplish this objective, it will be preferred that the sequencing of reactions be designed into the assay system such that the test sample need only to be contacted with a unitary test composition or test device.

As previously described, a convenient approach to reaction sequencing is to select subtractive and indicator reactions wherein if initiated simultaneously the subtractive reaction would be sufficiently rapid that it would be essentially complete before the indicator reaction could proceed to any significant extent. An assay system based on this relationship between the subtractive and indicator reactions can be presented in the form of a wide variety of test compositions and devices, but is particularly suited for use in a reagent strip. Such a test device comprises a carrier member or matrix, as is known in the art, incorporated with the subtractive and indicator reagents. Upon contact with the test sample, the reactions are initiated and the final detectable indicator response is characterized by the features of the present invention.

Another preferred approach involves compartmentalization of the reagents. A variety of test device configurations are available for ordering the sequence in which the test sample and resulting reaction mixtures come into contact with the subtractive and indicator reagents. In general principle, such devices comprise discrete compartments of reagents in fluid flow contact whereby the order to contact, and thus reaction, can be controlled. The compartments can be, for example, chambers capable of holding defined liquid volumes interconnected by capillary or other liquid conduit means, and the like.

A particularly useful device configuration based on compartmentalization is a reagent strip device comprising a carrier matrix having discrete zones incorporated with the respective reagents. In one form, such a device comprises multiple absorbent or porous layers incorporated with the reagents. The upper sample-contacting layer or layers comprise the elements of the subtractive reaction and lower layers into which the residue reaction mixture would diffuse comprise the elements of the indicator reaction. In another form, the device comprises an elongated absorbent carrier matrix having separate portions therealong incorporated with the reagents in their desired order to contact. The selected end of the matrix is contacted with the test sample and the reactions proceed as the liquid flows by capillarity, optionally with the aid of a developing fluid, along the device. Without further elaboration, it will be understood that a variety of test devices are possible and will be evident to the worker in the field to accomplish the objectives of the present invention.

The advantages of the present method are the result of the ability to controllably subtract a predetermined amount of analyte from the test sample prior to the indicator reaction. The subtraction reaction is controlled by the use of enzyme-catalyzed reactions involving a coreactant with the analyte. The amount of coreactant present at the initiation of the subtractive reaction and the stoichiometric relationship between the coreactant and analyte in the reaction dictates the amount of analyte consumed. The amount of coreactant desired in a given subtractive reaction will normally be determined empirically. Once the critical amount of coreactant is determined for a given test composition or system, it is a relatively simple matter to quantitatively and reproducibly add such amount in the manufacture of such a composition or test device.

The selection of the amount of coreactant in the test composition also depends on the desired effect in the assay. There are fundamentally two effects one can obtain by following the subtractive principle of the present invention—self-indication and improved visual resolution. In the case of self-indication, the amount of coreactant is selected to yield consumption of an amount of analyte sufficient to prevent generation of a particular indicator response unless the analyte is present at or above a preselected concentration in the sample. The indicator response that serves as the cut-off for the yes/no decision of the user commonly will be the threshold response that is detectable by the eye or by the instrument used. However, the cut-off response can be set at any selected level of response above such threshold, e.g., the appearance of a certain hue or saturation of color when observed visually or a certain level of absorbance when color is detected instrumentally.

The use of a single self-indicating test composition will inform the user only whether the analyte is present at or above a single preset analyte concentration. For broader quantitation, a series of test compositions comprising a varying amount of regulating coreactant will provide yes/no indicator responses at a variety of preset analyte concentrations. Any number of test device configurations suggest themselves. For example, test compositions which give the cut-off level of indicator response, e.g., the threshold detectable color, at increasing concentrations of analyte can be oriented in a fashion that numerical or other geometric shapes appear as the amount of analyte in the tested sample increases. As an illustration, a preselected first analyte concentration can be made sufficient to cause the formation of a colored area in the shape of the numeral "1" on the test device, and a second analyte concentration can be made sufficient to cause the formation of colored areas in the shape of the numerals "1" and "2", and so forth (see U.S. Pat. No. 4,042,329). As a further illustration, self-indicating test compositions that are sensitive to increasing analyte concentrations can be oriented on a test device to give a pin wheel or thermometer effect (see U.S. Pat. No. 4,654,310).

The improved resolution effect is obtained by varying the amount of coreactant in the test composition to find the amount of analyte that needs to be consumed to shift the indicator response into a region of optimal resolution over the desired range of analyte concentrations. The quantitation afforded by such a test composition is enhanced for those situations in which a single test composition is used and quantitation is dependent on resolving levels of indicator response, e.g., degree of color saturation.

The present invention will now be illustrated, but is not intended to be limited, by the following Examples.

EXAMPLE 1

This example demonstrates the linearity of the NADH subtractive reaction set out below:

NADH is a common product of enzymatic reactions involving analytes of diagnostic significance, e.g., glucose; therefore, such a subtractive reaction will serve as a useful means for generating self-indicating or improved resolution test systems in accordance with the present invention.

A mixture containing 0.57 mM NAD, 0.15 uM NADH, 0 to 0.167 mM sodium pyruvate, 0.67 units/mL diaphorase, 0 to 67 units/mL LDH, 0.5 mM iodonitrotetrazolium chloride (INT), and 0.1 M HEPES buffer, pH 7.5, in a total volume of 3 mL was incubated at 25° C. while monitoring absorbance at 504 nm (1 cm path length cell) in a Hewlett Packard Diode Array Spectrophotometer, Model 8451A. After establishing the color yield in the absence of subtractant, increasing amounts of sodium pyruvate were added to mixtures containing three different fixed concentrations of LDH (0.67, 6.7 and 67 U/mL). The absorbance after 5 minutes of incubation was subtracted from the absorbance obtained in the absence of subtractant and this difference plotted as a function of pyruvate concentration (FIG. 4).

Figure 4:
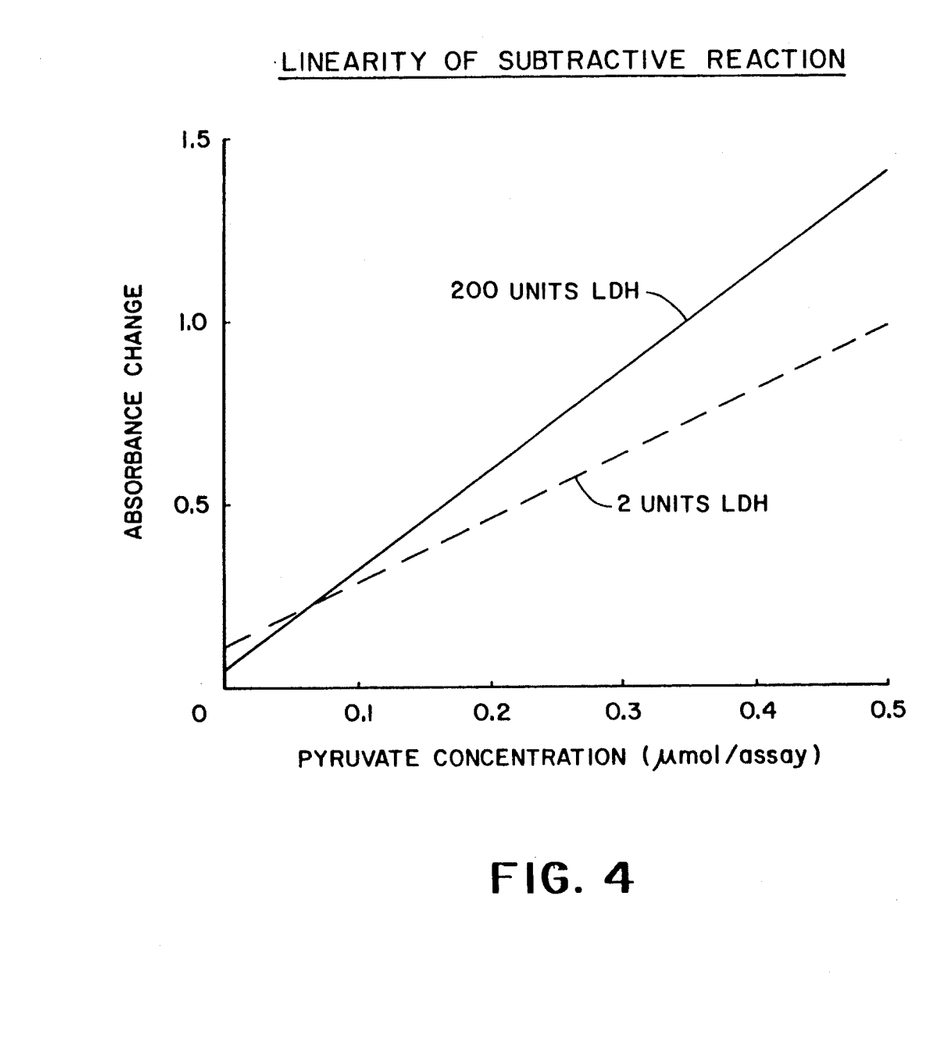
FIG. 4 is a graph showing the linearity of a particular subtractive reaction useful in the present invention as more particularly described and explained in the Examples.

FIG. 4 illustrates the effect of increasing amounts of subtractant (pyruvate) on the response of the liquid assay system described above. The ordinate represents the decrease in plateau absorbance achieved by the color forming reaction (INT transformed to formazan). The subtractive response is notably linear using 200 units of LDH. When the total amount of LDH in the assay mixture was reduced to 2 units (1:1 ratio to diaphorase activity), the linearity of the subtractive dose response was severely degraded. The slope obtained from the 200 units LDH curve in FIG. 4 corresponds to a subtraction which is about 45.3% of theoretical efficiency.

EXAMPLE 2

This example demonstrates the advantage of employing a subtractive reaction that is essentially irreversible. Irreversibility was conferred on the pyruvate/LDH subtractive reaction used in Example 1 by also carrying out the reaction:

Following the reaction conditions of Example 1, in this experiment pyruvate concentration was fixed at 0.1 mM, while the amount and ratio of LOX to LDH was varied according to Table 1:

TABLE 1

| Reaction No. | NADH | Pyruvate | LDH | LOX | Purpose |
|---|---|---|---|---|---|
| 1 | − | − | − | − | Control |
| 2 | + | − | − | − | NADH Cntrl. |
| 3 | + | − | − | − | NADH Cntrl. |
| 4 | + | + | 2 | − | Subtraction |
| 5 | + | + | 20 | − | Subtraction |
| 6 | + | + | 200 | − | Subtraction |
| 7 | + | + | 200 | 2 | Irrev.Subt. |
| 8 | + | + | 200 | 20 | Irrev.Subt. |
| 9 | + | + | 200 | 200 | Irrev.Subt. |

(Units/3 mL Assay)

Figure 5:
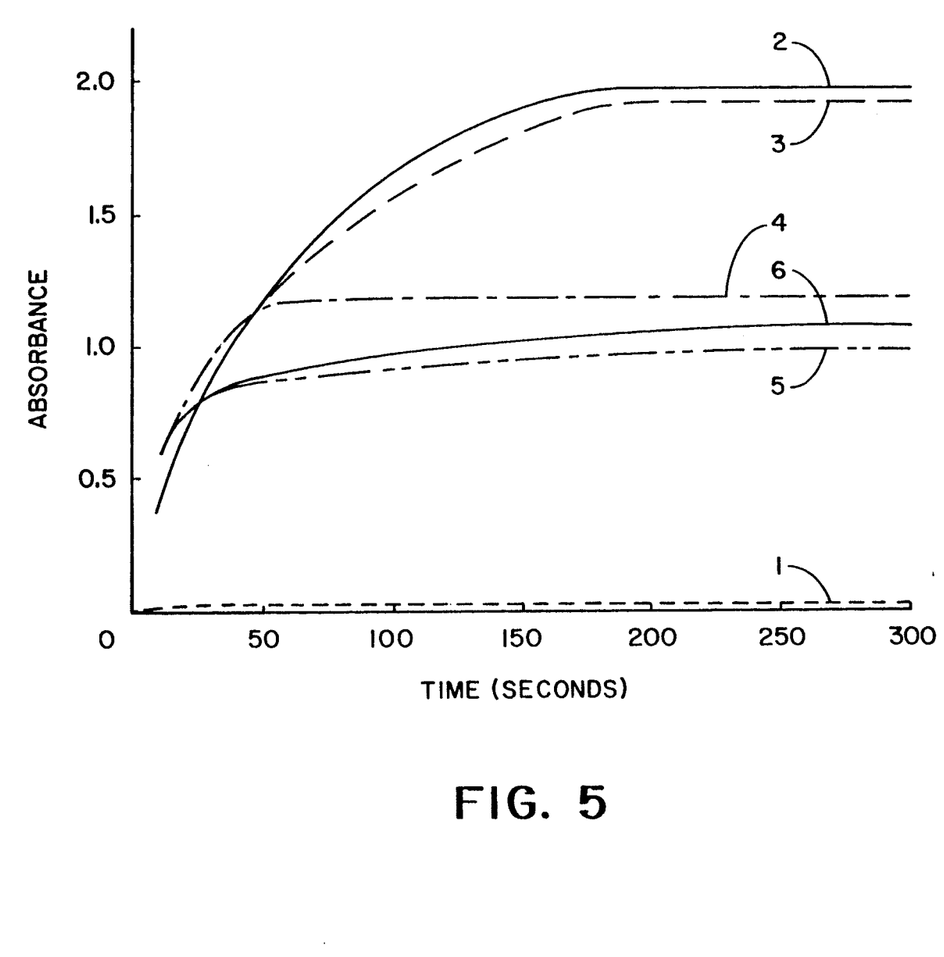
FIGS. 5 and 6 are graphs showing the effect of irreversibility in a particular subtractive reaction as more particularly described and explained in the Examples.
Figure 6:
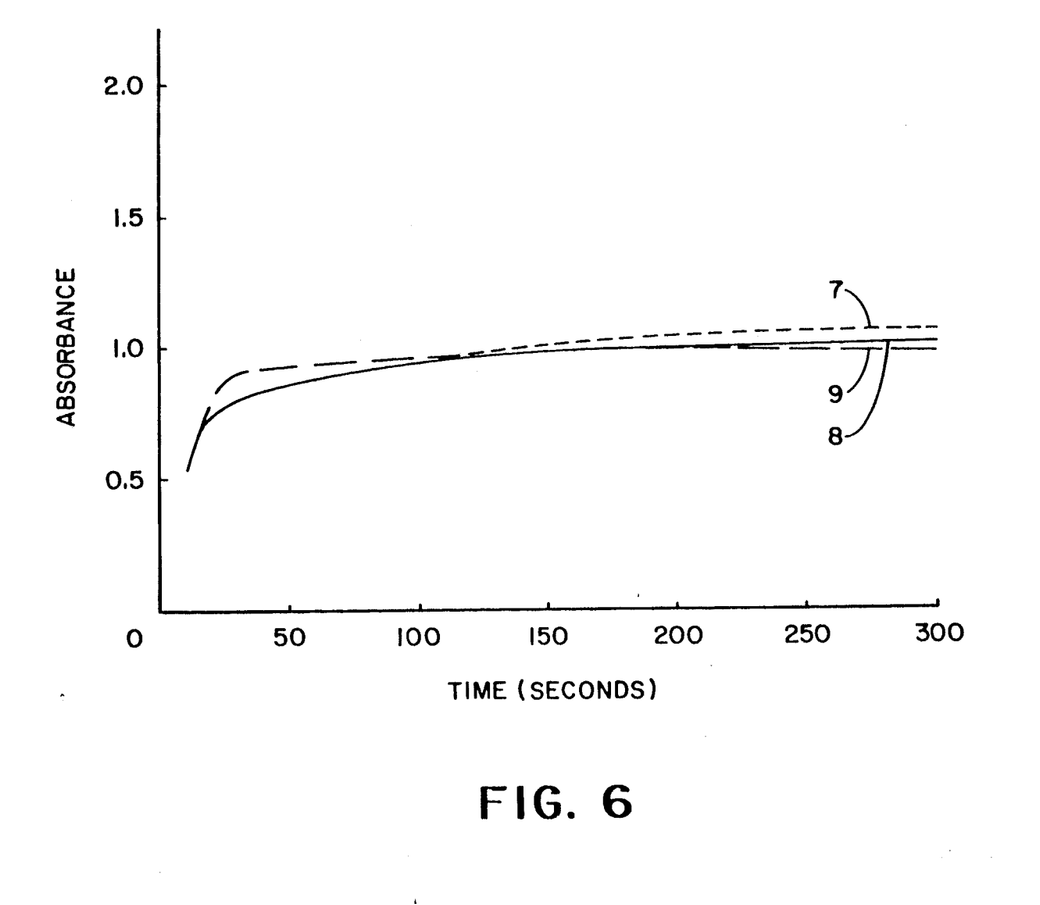

The results are shown in FIGS. 5 and 6. In the absence of LOX, higher levels of LDH resulted in increased upwards drift in plateau absorbance values (reactions 4–6). This drift presumably occurred by reversal of the LDH reaction to yield additional NADH once the color generation reaction exhausted the remainder after the initial subtraction reaction. However, increasing the concentration of LOX counteracted this trend and reduced drift (reactions 7–9 of FIG. 6).

EXAMPLE 3

Self-Indicating Assay

This example illustrates the formulation of a liquid assay system for glucose to produce self-indicating results.

A set of reaction mixtures are formulated containing adequate NAD (0.1 to 1.0 mM), varying concentrations of sodium pyruvate, quantities of glucose dehydrogenase and diaphorase sufficient to produce an endpoint indication within the desired time interval (0.5 to 5 minutes), a large excess of LDH (as compared to diaphorase activity) sufficient to assure completion of subtraction before significant color development occurs, at least twice as many units of lactate monooxygenase as LDH, 0.1 to 1.0 mM iodonitrotetrazolium chloride, and an appropriate buffer (for example, 0.1 HEPES, pH 7.5). The pyruvate concentrations are adjusted so that they are appropriate for removing amounts of NADH equivalent to the series of preselected glucose concentrations.

A convenient way of formulating this series of assay tubes is to combine all components into a fluid volume of 2.5 mL. Samples (0.5 mL) of a glucose-containing fluid are then added to each tube to bring the total volume to 3.0 mL. After mixing and incubation at room temperature for 30 seconds to 5 minutes, the presence or absence of red color is observed in each tube. The presence of significant coloration, as determined visually, indicates that the glucose concentration in the sample exceeds the preselected value for that given tube.

A set of typical results are illustrated as follows:

| Tube number: | 1 | 2 | 3 | 4 | 5 | 6 | 7 | 8 |
|---|---|---|---|---|---|---|---|---|
| [Glucose][1]: | 25 | 50 | 75 | 100 | 125 | 150 | 175 | 200 |
| Color: | +[2] | + | + | − | − | − | − | − |

[1] Preselected concentrations, determined by the concentration of pyruvate.
[2] A "+" means that the observed color production exceeds the threshold for visual detection, whereas "−" means that the tube appears to be essentially colorless.

From the results illustrated above, one concludes that the glucose concentration in the sample is between 75 and 100 mg/dL. The preselected glucose concentration values can be selected to provide as broad or as narrow a range of discrimination as desired.

EXAMPLE 4

Improved Resolution Assay

This example demonstrates how the area of optimal visual resolution can be shifted to different portions of the clinical glucose scale using a lipoamide/lipoamide dehydrogenase/DTPO subtraction reaction.

A test strip for glucose was prepared using a three layer gelatin-based film. The following reaction chemistries were incorporated into the film:

1)

2)

3)

GDH = glucose dehydrogenase
$LA_{ox}$ = lipoamide (oxidized form)
$LA_{red}$ = lipoamide (reduced form)
LADH = lipoamide dehydrogenase
DTPO = 2,2'-dithio-bis(pyridine-N-oxide)
INT = 2-(p-iodophenyl)-3-(p-nitrophenyl)-5-phenyltetrazolium chloride During the primary reaction within the film, glucose present within a sample reacts with NAD+ in the presence of glucose dehydrogenase to produce NADH and gluconolactone. The NADH product can either then reaction with the lipoamide in the subtraction scheme or react with INT and diaphorase to produce color. The concentration of DTPO present within the film determines the level of the color shift observed visually and instrumentally.

The film was prepared as follows:

| | Component | Quantity (grams) |
|---|---|---|
| 1st Layer: | gelatin (20%), pH 5.2 | 3.0 |
| | PVP (20%) | 1.0 |
| | Olin 10 G (4%) | 0.5 |
| | water | 5.5 |
| | INT | 0.065 |
| | PVP = polyvinylpyrolidone | |
| | Olin 10 G = alkylphenol alkoxylate surfactant (Olin Corp., Stamford, CT, USA) | |
| | Cast at 100 μ wet thickness. | |
| 2nd | gelatin (20%), pH 6.5 | 3.0 |
| Layer | PVP (20%) | 1.0 |
| | Olin 10 G | 0.5 |
| | MES buffer, 1M, pH 6.5 | 2.5 |
| | water | 3.0 |
| | GDH, 64 units/mg | 0.060 |
| | NAD+ | 0.060 |
| | BSA | 0.040 |
| | LADH, 132 units/mg | 0.200 |
| | diaphorase, 3.6 units/mg | 0.200 |
| | lipoamide and DTPO | |
| | film A = 0.0 LA; 0.0 DTPO | |
| | film B = 0.080 g LA; 0.0 DTPO | |
| | film C = 0.050 g LA; 0.010 g DTPO | |
| | film D = 0.050 g LA; 0.020 g DTPO | |
| | film E = 0.050 g LA; 0.030 g DTPO | |
| | MES = 2-(N-morpholino)ethane sulfonic acid | |
| | BSA = bovine serum albumin | |
| | Cast at 100 μ wet thickness | |
| 3rd layer | carbodiimide | 0.125 |
| | Olin 10 G (4%) | 0.250 |
| | water | 9.625 |
| | carbodiimide = 1-ethyl-3-(3-dimethyl-aminopropyl) carbodiimide | |
| | cast at 24 μ wet thickness | |

The components of the first layer were combined in a flask at 40°–45° C. in the order given and allowed to stir for at least 15 minutes. The solution was then degassed and coated on a PET film base [Agfa-Gevaert A. G., Leverkusen, West Germany] at a 100 μ wet thickness. Films were dried in an oven at 40° C. Likewise the second solution was mixed, degassed and coated at 100 μ wet thickness over the first layer. The film was then dried in an oven at 40° C. The third layer was mixed at room temperature and coated over the first and second layer at a wet thickness of 24μ. The film was then dried in an oven at 40° C. The third layer crosslinks the gelatin which then allows the sample to be removed from the surface of the film. Films were cut into strips and then reacted with glucose samples for 15 seconds. After removal of sample from their surface, the strips were placed in a Macbeth 1500/Plus Quick Key Color spectrophotometer (Kollmorgan Corp., Newburgh, N.Y., USA) for analysis.

The Macbeth spectrophotometer collects reflectance data of the reacted strips at 16 different wavelengths. These data are then converted into the three dimensional color space coordinates for each strip. Each color can then be represented by its color space coordinates $L^*$, $a^*$, and $b^*$. Distances between any two colors in CIELAB color space ["Color in Business, Science, and Industry", 3rd ed., Judd and Wyszecki (1975), p. 320] are represented by the formula:

$$\Delta E = \sqrt{(L^*_1 - L^*_2)^2 + (a^*_1 - a^*_2)^2 + (b^*_1 - b^*_2)^2}$$

where $L_1^*$, $a_1^*$, and $b_1^*$ are color coordinates of sample 1 and $L_2^*$, $a_2^*$, $a_2^*$, $b_2^*$ are the color coordinates for sample 2. Consequently the larger the $\Delta E$ value the larger the difference between the two colors. Generally speaking, a $\Delta E$ of at least 5 units is needed for most observers to distinguish differences between colors. However, this changes depending on the color and the observer.

Figure 7:
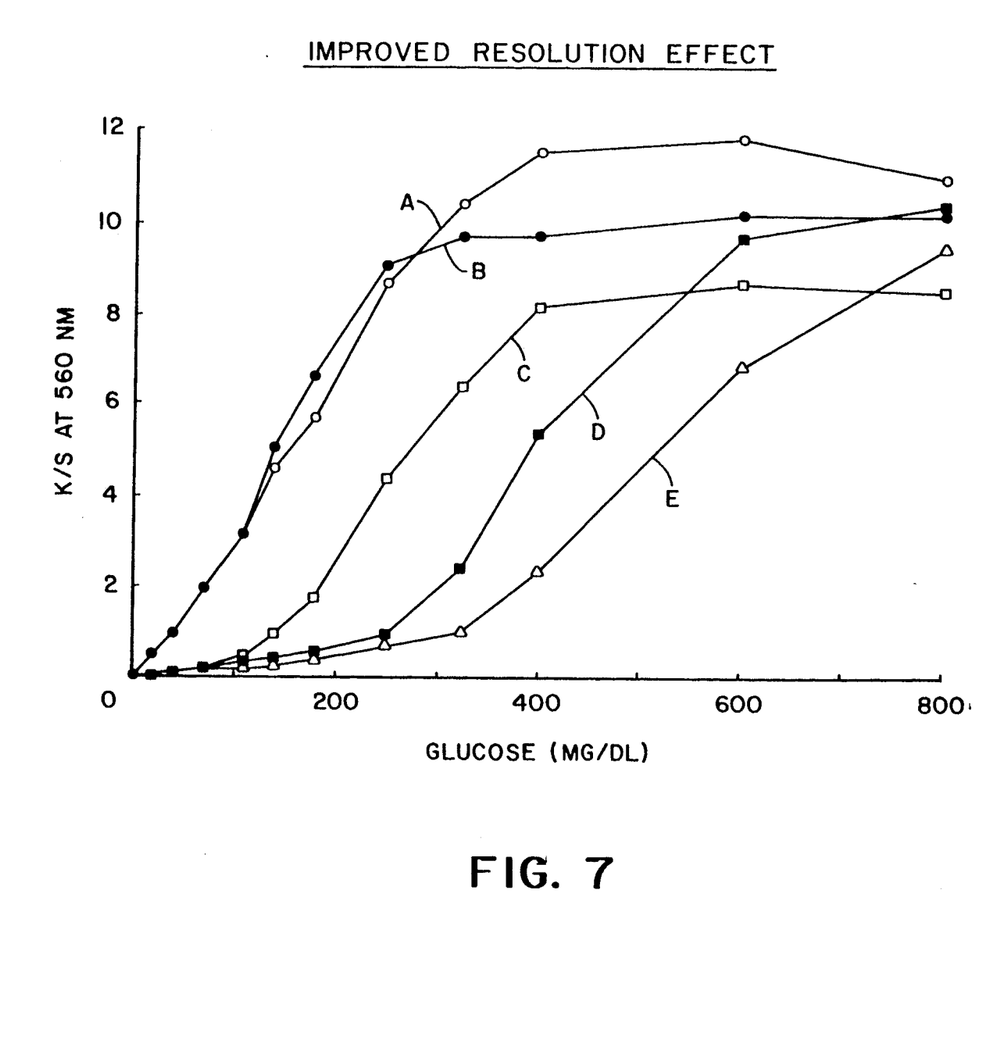
FIG. 7 is a graph showing the results of a study of the effect of a subtractive reaction on the present invention on visual resolution of a color producing reagent strip.

Based on this knowledge of $\Delta E$'s, Table 2 below shows the color differences between glucose levels for each of the films made above. This table shows how the area of best visual resolution has shifted as a function of the increasing concentration of the DTPO component. Note the absence of a shift in visual resolution of the film (B) when Lipoamide and LADH are present without DTPO. Therefore using the lipoamide, LADH, and DTPO subtraction method the area of best visual resolution can be shifted to different areas of the clinical glucose range. This is further illustrated in FIG. 7. In this graph the spectral reactivity curves for each of the films are represented. One can see that both the initial INT curve (Film A) and the Lipoamide curve (Film B) follow the same path. When DTPO is added along with Lipoamide and LADH, a shift in the spectral curves can be seen (Films C, D, E). In addition, this system has now been made irreversible. This subtraction chemistry scheme may be applied to other analytes which produce NADH in one of its initial reactions.

TABLE 2

Comparision of Films

| Glucose Levels (mg/dL) | ΔE's Between Glucose Levels Films | | | | |
|---|---|---|---|---|---|
| | A | B | C | D | E |
| 0–20 | 21.8 | 20.7 | 6.0 | 5.0 | 4.6 |
| 20–40 | 8.9 | 11.2 | 3.5 | 2.9 | 2.9 |
| 40–70 | 10.7 | 9.4 | 6.4 | 4.9 | 5.1 |
| 70–110 | 6.4 | 7.4 | 7.6 | 5.0 | 1.6 |
| 110–140 | 5.0 | 5.9 | 10.9 | 3.9 | 3.1 |
| 140–180 | 3.0 | 3.3 | 9.1 | 3.5 | 3.6 |
| 180–250 | 5.6 | 4.9 | 12.6 | 7.9 | 6.8 |
| 250–325 | 4.3 | 2.6 | 5.1 | 13.9 | 5.2 |
| 325–400 | 6.0 | 1.6 | 2.9 | 10.7 | 12.2 |
| 400–600 | 2.0 | 2.7 | 0.9 | 9.9 | 14.1 |
| 600–800 | 1.5 | 1.5 | 0.3 | 4.5 | 7.2 |

Underlined ΔE's denote optimal visual resolution

The present invention has been particularly described and exemplified above. Obviously, many other variations and modifications of the invention can be made without departing from the spirit and scope thereof.

What is claimed is:

1. An analytical method for the spectrophotometric determination of glucose at a predetermined concentration in a liquid test sample which comprises the steps of:
   a) combining the glucose containing sample with NAD and glucose dehydrogenase under conditions which will result in the transformation of the NAD to NADH;
   b) simultaneously providing pyruvate and lactate dehydrogenase to convert the NADH formed in step (a) to NAD and the pyruvate to lactate, with the amount of pyruvate present upon initiation of the reaction being equal to the amount of glucose that would be present in the test sample at said predetermined concentration to be determined, multiplied by the stoichiometric ratio of moles of NADH per mole of glucose consumed in step (a); and
   c) determining whether any NADH remains in the reaction mixture from step (a) by measuring light absorbance of NADH or a product of an indicator reaction involving NADH.

2. The method of claim 1 wherein remaining NADH is determined by measurement of absorbance at 340 nm.

3. The method of claim 1 wherein the remaining NADH is determined by an oxidation-reduction reaction that produces a colored indicator product which is detected visually or by instrumental means.

4. The method of claim 3 wherein the oxidation-reduction reaction involves the reaction of NADH with a tetrazolium salt in the presence of diaphorase to convert the tetrazolium salt to its corresponding formazan.

5. The method of claim 1 wherein there is provided oxygen and lactate monooxygenase to convert the lactate formed by the reaction of the pyruvate, lactate dehydrogenase and NADH to acetate and carbon dioxide thereby rendering this reaction irreversible.

6. A test composition for the determination of the presence of glucose at a predetermined concentration in a test sample by the measurement of a particular indicator response, which composition comprises:
   a) pyruvate and lactate dehydrogenase which react with NADH to convert it to NADH while converting the pyruvate to lactate;
   b) glucose dehydrogenase and NAD wherein the amount of pyruvate and lactate dehydrogenase is stoichiometrically sufficient to convert a predetermined is stoichiometrically sufficient to convert a predetermined amount of NADH formed by the glucose dehydrogenase catalyzed reaction of glucose with NAD back to the undetectable NAD, said predetermined amount of pyruvate and lactate dehydrogenase being sufficient to inhibit the formation of detectable NADH unless the glucose level in the test sample is greater than said predetermined concentration.

7. The composition of claim 6 wherein there is included monooxygenase which, in the presence of oxygen, will convert the lactate to acetate and carbon dioxide.

8. The test composition of claim 6 wherein there is included an indicator which exhibits a detectable response upon reaction with NADH.

9. The composition of claim 8 in which the indicator is a tetrazolium salt and there is included in the composition diaphorase so that NADH generated in excess of that which is converted back to NAD by its lactate dehydrogenase catalyzed reaction with pyruvate will, in the presence of the diaphorase, convert the tetrazolium salt to its colored formazan thereby providing a detectable response.

* * * * *